US011735066B2

United States Patent
Fiore et al.

(10) Patent No.: US 11,735,066 B2
(45) Date of Patent: *Aug. 22, 2023

(54) TEST BENCH ASSEMBLY FOR THE SIMULATION OF CARDIAC SURGERY AND/OR INTERVENTIONAL CARDIOLOGY OPERATIONS AND/OR PROCEDURES

(71) Applicants: POLITECNICO DI MILANO, Milan (IT); UNIVERSITA' DEGLI STUDI DI MILANO, Milan (IT)

(72) Inventors: Gianfranco Beniamino Fiore, Milan (IT); Alberto Cesare Luigi Redaelli, Milan (IT); Riccardo Vismara, Milan (IT); Carlo Antona, Milan (IT); Guido Gelpi, Milan (IT); Massimo Giovanni Lemma, Milan (IT); Andrea Mangini, Milan (IT)

(73) Assignees: POLITECNICO DI MILANO, Milan (IT); UNIVERSITA' DEGLI STUDI DI MILANO, Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/560,553

(22) Filed: Dec. 23, 2021

(65) Prior Publication Data
US 2022/0157197 A1    May 19, 2022

Related U.S. Application Data

(63) Continuation of application No. 16/349,875, filed as application No. PCT/IB2017/057098 on Nov. 14, 2017, now Pat. No. 11,238,755.

(30) Foreign Application Priority Data
Nov. 14, 2016  (IT) ..................... IT102016000114762

(51) Int. Cl.
  *G09B 23/30*   (2006.01)
  *A01N 1/02*    (2006.01)
  *A61B 17/00*   (2006.01)

(52) U.S. Cl.
  CPC ......... *G09B 23/303* (2013.01); *A01N 1/0247* (2013.01); *G09B 23/30* (2013.01); *G09B 23/306* (2013.01); *A61B 2017/00716* (2013.01)

(58) Field of Classification Search
  CPC ....... G09B 23/28; G09B 23/30; G09B 23/303
  See application file for complete search history.

(56) References Cited

U.S. PATENT DOCUMENTS 5,634,797 A   6/1997  Montgomery
5,807,737 A   9/1998  Schill et al.
(Continued)

OTHER PUBLICATIONS

International Search Report and Written Opinion of the International Searching Authority for International Patent Application No. PCT/IB2017/057098 dated Jan. 16, 2019, 7 pages.
(Continued)

*Primary Examiner* — Kurt Fernstrom
(74) *Attorney, Agent, or Firm* — Sughrue Mion, PLLC (57) ABSTRACT

A test bench assembly for simulating cardiac surgery includes a passive heart having at least one pair of cardiac chambers with an atrial chamber and a ventricular chamber. A reservoir is adapted to house working fluid. A pressure generator fluidically connects both to the ventricular chamber of the passive heart and to the reservoir. A pressure regulation device provides working fluid in input to the atrial chamber with preload pressure, and working fluid in output from the ventricular chamber with afterload pressure. The pressure regulation device fluidically connects both to the atrial chamber of the passive heart and to the ventricular chamber of the passive heart. The pressure regulation device
(Continued)

has a single compliant element for each pair of cardiac chambers, which provides working fluid with both preload, and afterload pressures.

21 Claims, 6 Drawing Sheets

(56) References Cited

U.S. PATENT DOCUMENTS

| | | |
|---|---|---|
| 6,790,043 B2 | 9/2004 | Aboud |
| 8,608,484 B2 | 12/2013 | Kalafut et al. |
| 8,678,830 B2 | 3/2014 | Gurdin et al. |
| 9,460,640 B2 | 10/2016 | Lee |
| 9,881,523 B2 | 1/2018 | Sweeney |
| 10,229,615 B2 * | 3/2019 | Carson .................. G09B 23/32 |
| 2007/0054256 A1 | 3/2007 | Low et al. |
| 2010/0323339 A1 | 12/2010 | Ritchie |
| 2011/0217684 A1 | 9/2011 | Park et al. |
| 2013/0288218 A1 | 10/2013 | Mallin et al. |
| 2014/0099620 A1 | 4/2014 | Lee |
| 2014/0370490 A1 | 12/2014 | Taizzo et al. |
| 2015/0024362 A1 | 1/2015 | Feins et al. |
| 2018/0108276 A1 | 4/2018 | Ishiyama et al. |

OTHER PUBLICATIONS

Richards, A. et al., "A Dynamic Heart System to Facilitate the Development of Mitral Valve Repair Techniques", Annals of Biomedical Engineering, 37(4): 651-660 (2009).

* cited by examiner

TEST BENCH ASSEMBLY FOR THE SIMULATION OF CARDIAC SURGERY AND/OR INTERVENTIONAL CARDIOLOGY OPERATIONS AND/OR PROCEDURES

CROSS-REFERENCE TO RELATED APPLICATIONS

This application is a Continuation of U.S. patent application Ser. No. 16/349,875 filed May 14, 2019, which is a National Stage of International Application No. PCT/IB2017/057098 filed Nov. 14, 2017, which claims priority based on Italian Patent Application No. 102016000114762 filed Nov. 14, 2016, the contents of all of which are incorporated herein by reference in their entirety.

FIELD OF THE INVENTION

The present invention relates to a test bench assembly for the simulation of cardiac surgery and/or interventional cardiology operations and/or procedures.

BACKGROUND ART

One of the purposes of training for cardiac surgeons and for interventional cardiologists is to provide clinical personnel with a certain familiarity and acquaintance with the particular physiological conditions they will have to confront in the course of an intervention which involves the beating heart of a living patient. The aspects which can mainly interfere with the intervention of the clinical operator are of a fluid dynamic nature and due to blood circulation, to the opening and closing of the heart valves and to the deformation of the organ during the cardiac cycles. Hence, there is a need to provide a test bench able to faithfully replicate the physiological conditions of the cardiac cycle.

The four cardiac chambers comprise two atria and two ventricles, in which each atrium receives the blood coming from body tissues and flows in a ventricle which in turn flows in an artery. The left atrium and the left ventricle, separated by the mitral valve, form the left heart, which receives blood from the lungs and pumps it in the body, while right atrium and right ventricle form the right heart which receives blood from the body and transmits it to the lungs.

Generally, known test benches comprise a heart from a human or animal donor, for example hearts of porcine origin. This heart is generally explanted by cutting the blood vessels directly connected to the atria and to the ventricle but leaving intact a section of the veins and of the arteries as well as the native cardiac valves. Such an explanted heart is incapable of contracting spontaneously to pressurize the fluid received in the cardiac chambers which determines the opening of the cardiac valves to carry out the pumping action for which it is intended in vivo. Therefore, said explanted heart is connected to a pumping system provided in the test bench and comprising one or more pulsatile pumps, as well as a system of hydraulic conduits and containers which simulate the hydraulic impedances out of the heart and into the heart.

Usually, the pumping system is connected to the explanted heart by making a hole in the wall of the heart, usually in the apical portion of the heart, and providing a conduit which flows directly into the ventricular chamber. Through this piping the pumping system pressurizes fluid within the ventricular chamber to determine the opening of the aortic outflow valve, out of the left ventricle. Downstream of the aortic valve out of the left ventricle, a piping is provided being connected to a hydraulic impedance and an afterload container, in order to simulate the systemic impedance seen by the heart when it ejects the blood.

Known test bench solutions have been designed to model by means of a system of four impedances and four respective containers both the fluid dynamic impedance which the heart sees during the ejection of blood from the ventricle, known as afterload, and the pressure due to the blood returning to the atria, known as preload. In these known solutions, it has been opted to realize as many impedance simulation systems as there are cardiac chambers, because the preload pressure of the fluid flowing into the atria is far lower than the afterload pressure which the blood sees in ejection. For example, solutions of this type are shown in the documents US-2011-0217684, US-2013-0288218, US-2014-0370490, US-2014-0099620, US-2015-0024362 and the non-patent disclosure Andrew L. Richards et al.: "A Dynamic Heart System to Facilitate the Development of Mitral Valve Repair Techniques" (ANNALS OF BIOMEDICAL ENGINEERING, KLUWER ACADEMIC PUBLISHERS-PLENUM PUBLISHERS, NE, Vol. 37 No. 4. 18 Feb. 2009).

Solutions of this kind impose large dimensions of the test bench and require the presence of highly qualified personnel to manage them during the installation and utilization of the test bench. These aspects make the test bench difficult to transport, forcing the heart surgeon to go to the place where the test bench is installed. At the same time, this type of test benches is substantially impossible to put in operation without the intervention of specialized technical personnel, forcing the technical personnel to go to the place where the test bench is installed.

Thus, there is a strongly felt need to provide a test bench solution which faithfully reproduces the physiological conditions without thereby being bulky or complicated to operate.

There is a need to provide a test bench solution which allows to reduce the installation and operation costs of the test bench compared to known solutions, without thereby resulting in diminished functionality or reliability.

There is a need to provide a test bench with a reduced number of components and with reduced size compared to known solutions, without thereby resulting in diminished functionality or reliability.

There is a strongly felt need to provide a test bench solution which faithfully reproduces the physiological conditions while allowing to reduce the costs associated with the procedures for training the heart surgeon/interventional cardiologist.

Solution

It is one object of the present invention to overcome the drawbacks of the prior art mentioned hitherto and to provide a solution to the needs stated with reference to the background art.

This and other objects are achieved by an assembly according to claim 1.

Some advantageous embodiments are set forth in the dependent claims.

According to an aspect of the invention, a test bench assembly for the simulation of cardiac surgery and/or interventional cardiology operations comprises: a passive heart, in which said passive heart is an explanted or artificial or hybrid heart, said passive heart having at least one pair of cardiac chambers, comprising an atrial chamber and a ventricular chamber;

a reservoir, adapted to house the working fluid; a pressure generator, adapted to provide the pumping function to said passive heart by pumping said working fluid, said pressure generator being fluidically connected both to at least one ventricular chamber of said passive heart and to said reservoir by means of first fluid connection means; a pressure regulation device which provides the working fluid in input to the atrial chamber with the preload pressure, and the working fluid in output from the ventricular chamber with the afterload pressure, said pressure regulation device being fluidically connected both to said atrial chamber of said passive heart and to said ventricular chamber of said passive heart by means of second fluid connection means.

According to an aspect of the invention, said pressure regulation comprises a single compliant element for each pair of cardiac chambers, which provides the working fluid with both the preload and the afterload pressures.

According to an aspect of the invention, said pressure generator comprises at least one flow intercepting element, for example a solenoid valve, which selectively allows direct fluid connection between said passive heart and said reservoir.

According to an aspect of the invention, said pressure generator comprises a kinetic stationary flow rate pump, for example a centrifugal pump.

According to an aspect of the invention, said first fluid connection means comprise at least one conduit which flows into the interior of said ventricular chamber of the passive heart, and said conduit comprises an anchoring plug which can be fitted by acting only from the exterior of said ventricular chamber. For example, said anchoring plug comprises a deformable anchoring device adapted to elastically deform to fit into an inlet opening formed in the heart wall which delimits the ventricular chamber of the passive heart to be engaged in undercut against a face of the heart wall arranged in undercut with respect to the outer face of the passive heart.

DRAWINGS

Further features and advantages of the invention shall become readily apparent from the following description of preferred embodiments thereof, provided by way of non-limiting example, with reference to the accompanying drawings, in which:

FIG. 1 *bis* is a diagrammatic depiction of a test bench assembly, in accordance with one embodiment;

DESCRIPTION OF SOME PREFERRED EMBODIMENTS

In accordance with a general embodiment, a test bench assembly 10 is provided for the simulation of cardiac surgery and/or interventional cardiology operations and/or procedures. Said test bench assembly 10 is particularly suitable to enable the execution of prosthesis tests, tests of new surgical therapies and the training of a cardiac surgeon/interventional cardiologist, avoiding acting on a living being.

Said test bench assembly 10 comprises a passive heart 12. Said passive heart 12 is an explanted or artificial or hybrid heart. For example, said passive heart 12 is a heart from an animal donor, for example porcine or ovine, or it is a heart from a human donor, or it is an artificial heart. The term "passive" means that said heart does not carry out the pumping action spontaneously. Said passive heart 12 has at least one pair of heart chambers 14, 16; 114, 116, said pair of cardiac chambers comprising one atrial chamber 14; 114 and one ventricular chamber 16; 116.

In accordance with one embodiment, said passive heart 12 comprises at least one heart valve 18; 19; 118. Said heart valve 18; 19; 118 is a native valve, or it is an artificial valve, or it is a hybrid valve. For example, said heart valve 18; 118 is a mitral valve 18, interposed between left atrial chamber 14 and left ventricular chamber 16. In this case, said test bench assembly 10 simulates the left heart.

Preferably, said heart valve 18; 19; 118 is an outflow valve 19, preferably an aortic valve 19 positioned at the output from the left ventricular chamber 16. In accordance with one embodiment, said cardiac valve is an outflow valve 19, preferably a pulmonary valve, positioned at the output from the right ventricular chamber 116. In accordance with one embodiment, said passive heart 12 comprises at least one section of blood vessel. In accordance with one embodiment, said passive heart 12 comprises a section of aorta and a cardiac valve 19 positioned between the left ventricular chamber 16 and the section of aorta, to simulate the aortic valve. Preferably, said passive heart 12 comprises at least one outflow valve 19 positioned downstream of a ventricular chamber of the passive heart 12, for example positioned in said at least one section of blood vessel. Preferably, said outflow valve 19 is adapted to selectively allow the flow of the working fluid 72 out of the ventricular chamber of said at least one pair of cardiac chambers of the passive heart 12.

For example, said passive heart 12 comprises a section of aortic arch, or a section of pulmonary artery, or it comprises a section of vena cava. In accordance with one embodiment, said passive heart 12 comprises two pairs of heart chambers 14, 16, 114, 116 each comprising one atrial chamber 14; 114 and one ventricular chamber 16; 116, an interatrial septum 68 which divides the atrial chambers 14, 114 and an interventricular septum 70 which divides the ventricular chambers 16, 116, one heart valve 18; 118 interposed between each atrial chamber 14; 114 and each ventricular chamber 16; 116 and sections of blood vessels connected to each of the ventricular chambers 16; 116.

Said test bench assembly 10 further comprises a reservoir 20, adapted to house the working fluid 72. Preferably, said working fluid 72 is a liquid. For example, said working fluid 72 is a liquid having the viscosity of blood. For example, said working fluid 72 is water or an aqueous solution. The provision of such a test bench assembly 10 to simulate cardiac surgery and/or interventional cardiology operations avoiding the need to use blood as a working fluid 72.

Said test bench assembly 10 further comprises a pressure generator 22, adapted to provide the pumping function to said passive heart 12 by pumping said working fluid 72, Said pressure generator 22 is fluidically connected both to said ventricular chamber 16 of said passive heart 12 and to said reservoir 20 by means of first fluid connection means 66.

Said test bench assembly 10 further comprises at least one pressure regulation device 24 which provides the working fluid 72 in input to the atrial chamber 14 with the preload pressure and the working fluid in output from the left ventricular chamber 16 with the afterload pressure. Preferably, said at least one pressure regulation device 24 provides the working fluid 72 in input to the left atrial chamber 14 with the preload pressure, and the working fluid in output from the left ventricular chamber 16 and downstream of the outflow valve 19, for example the aortic valve 19, with the afterload pressure.

Said at least one pressure regulation device 24 is fluidically connected both to said left atrial chamber 14 of said passive heart 12 and to said left ventricular chamber 16 of said passive heart 12 by means of second fluid connection means 64.

In accordance with one embodiment, said test bench assembly 10 further comprises at least one additional pressure regulation device 124 which provides the working fluid in input to the right atrial chamber 114 with the preload pressure, and the working fluid at the output from the right ventricular chamber 116 with the afterload pressure, in which said at least one additional pressure regulation device 124 is fluidically connected both to said right atrial chamber 114 of said passive heart 12 and to said right ventricular chamber 116 of said passive heart 12 by means of second fluid connection means 64. Preferably, said at least one additional pressure regulation device 124 provides the working fluid 72 in input to the right atrial chamber 114 with the preload pressure, and the working fluid 72 at the output from the right ventricular chamber 116 and downstream of the outflow valve, for example the pulmonary valve, with the afterload pressure.

Said at least one pressure regulation device 24 allows to regulate the pressure of the working fluid both at the input and at the output from the passive heart 12, to simulate the fluid dynamic impedance of the preload and afterload pressures observed in vivo.

In accordance with a preferred embodiment, said at least one pressure regulation device 24 comprises a single compliant element 26 for each pair of cardiac chambers 14, 16; 114, 116, which provides the working fluid 72 with both the preload and the afterload pressures. Preferably, said compliant element 26 is a container.

Advantageously, said single compliant element 26 for each pair of heart chambers 14, 16 provides the working fluid 72 with both the preload and the afterload pressures while having reduced size compared to known solutions which instead use a first compliant element to provide the preload and a second compliant element to provide the afterload pressure. This allows to make the test bench assembly 10 easily transportable.

The provision of a transportable test bench assembly 10 allows to reduce the operating costs of the test bench, because it is not necessary for clinical personnel, who generally have high hourly costs, to travel to the place where the test bench assembly 10 is installed, but it allows to take the test bench to the place where the clinical personnel is located. In accordance with one embodiment, said test bench assembly 10 comprises a support dolly comprising wheels, so as to facilitate transporting said test bench assembly 10.

With additional advantage, said single compliant element 26 for each pair of heart chambers 14, 16; 114, 116 allows to provide a pressure regulation device 24 which self-regulates at steady state. This allows to avoid associating electronic sensors and/or control devices with the at least one pressure regulation device 24; 124. In other words, the provision of such a single compliant element 26 for each pair of cardiac chambers 14, 16; 114, 116 allows to provide a self-controlled pressure regulation device 24.

In accordance with one embodiment, said compliant element 26 acts as an expansion vessel or tank. Preferably, the hydrostatic head of said compliant element 26 varies when using the test bench assembly 10 to allow the circuit to self-regulate.

In accordance with a preferred embodiment, said at least one pressure regulation device 24 comprises an afterload resistance 30 which regulates the afterload pressure. By way of non-limiting example, the afterload pressure is between approximately 50 mmHg (millimeters of mercury) equivalent to approximately 67 millibar and approximately 100 mmHg equivalent to approximately 133 millibar, and the preload pressure is between approximately 5 mmHg equivalent to approximately 7 millibar and approximately 15 mmHg equivalent to approximately 20 millibar.

The provision of said afterload resistance 30 allows to generate a systolic pressure in the ventricular chamber 16; 116, for example the left ventricular chamber 16 of the left heart, which is higher than the afterload pressure, so that the mitral valve 18 closes during the systolic phase.

In accordance with one embodiment, said second fluid connection means 64 comprise a systole branch 32 which fluidically connects, through said outflow valve, for example said aortic valve 19, said ventricular chamber 16; 116 of said passive heart 12 to said at least one pressure regulation device 24; 124, and a diastole branch 34 which fluidically connects said at least one pressure regulation device 24; 124 to said at least one atrial chamber 14; 114 of said passive heart 12. In accordance with one preferred embodiment, said pressure regulation device 24 allows to regulate pressure in the segment of the systole branch 32 which is between the outflow valve 19 and the afterload resistance 30, both when the aortic valve 19 is closed and when the aortic valve 19 is open. Preferably, said segment of the systole branch 32 which is between the outflow valve 19 and the afterload resistance 30 is positioned downstream of the outflow valve 19, or aortic valve 19, along said systolic path S-S.

In accordance with one embodiment, said systole branch 32 comprises said afterload resistance 30.

In accordance with one embodiment, said systole branch 32 and said diastole branch 34 join in a section 46 which flows into said compliant element 26.

In accordance with one embodiment, said compliant element 26 is a free surface vessel. In accordance with one embodiment, said compliant element 26 is a closed pressurized tank.

Preferably, the working fluid in said compliant element 26 has higher pressure than the working fluid in said reservoir 20. The provision of such a pressure gradient favorably allows to determine a movement by gravity of the working fluid towards said reservoir 20. Thereby, it is possible to simulate the diastole phase in a passive manner, in other words avoiding supplying energy to determine the movement of the working fluid along the diastolic path D-D.

In accordance with one preferred embodiment, said compliant element 26 is a free surface vessel and it is positioned higher than said passive heart 12 which in turn is positioned lower than said reservoir 20. In this way, it is possible to maintain the working fluid under pressure, preventing air from entering into the fluid when the test bench assembly 10 is not in use.

A first height difference z1 between the hydrostatic head of said compliant element and said passive heart 12, and a second height difference z2 between said passive heart 12 and the hydrostatic head of said reservoir 20, and a third height difference z3 between the hydrostatic head of said compliant element 26 and the hydrostatic head of said reservoir 20. Preferably, said first height difference z1 is equal to the sum of said second height difference and of said third height difference z2+z3.

In accordance with a preferred embodiment, said pressure generator 22 comprises at least one flow intercepting element 28, which selectively enables direct fluid connection between said passive heart 12 and said reservoir 20.

Preferably, said at least one flow intercepting element 28 comprises at least one active valve. Preferably, said at least one active valve is at least one solenoid valve. The provision of a solenoid valve allows to obtain rapid response times of the fluid intercepting element 28.

In accordance with an embodiment, said flow intercepting element 28 comprises a two-way solenoid valve. In accordance with an embodiment, said flow intercepting element 28 comprises a three-way solenoid valve.

In accordance with an embodiment, said active valve is a hydraulic control valve. In accordance with an embodiment, said active valve is a pneumatic control valve.

In accordance with a preferred embodiment, said pressure generator 22 comprises a kinetic stationary flow rate pump 48. The provision of a kinetic stationary flow rate pump 48, which cooperates with a flow intercepting element 28 allows to simulate the pressures of the cardiac cycle, without thereby using a programmable pulsatile pump. In this way, a simplified activation of the test bench is allowed, as well as a simplified control in operating conditions, which allows even operators who are not qualified in engineering matters to control the activation and operation of the test bench. This allows to reduce the operating costs of the test bench.

In accordance with an embodiment, said first fluid connection means 66 comprise a reservoir conduit 74, which fluidically connects said reservoir 20 to said pressure generator 22, said reservoir conduit 74 flowing by means of a bifurcation 76 into a pump branch 78, which flows into said kinetic stationary flow rate pump 48, and a shunt branch 80, which flows into said flow intercepting element 28 avoiding traversing said kinetic stationary flow rate pump 48. Preferably, said kinetic stationary flow rate pump 48 is fluidically connected to said flow intercepting element 28 by means of a generator conduit 82.

Figure 1:
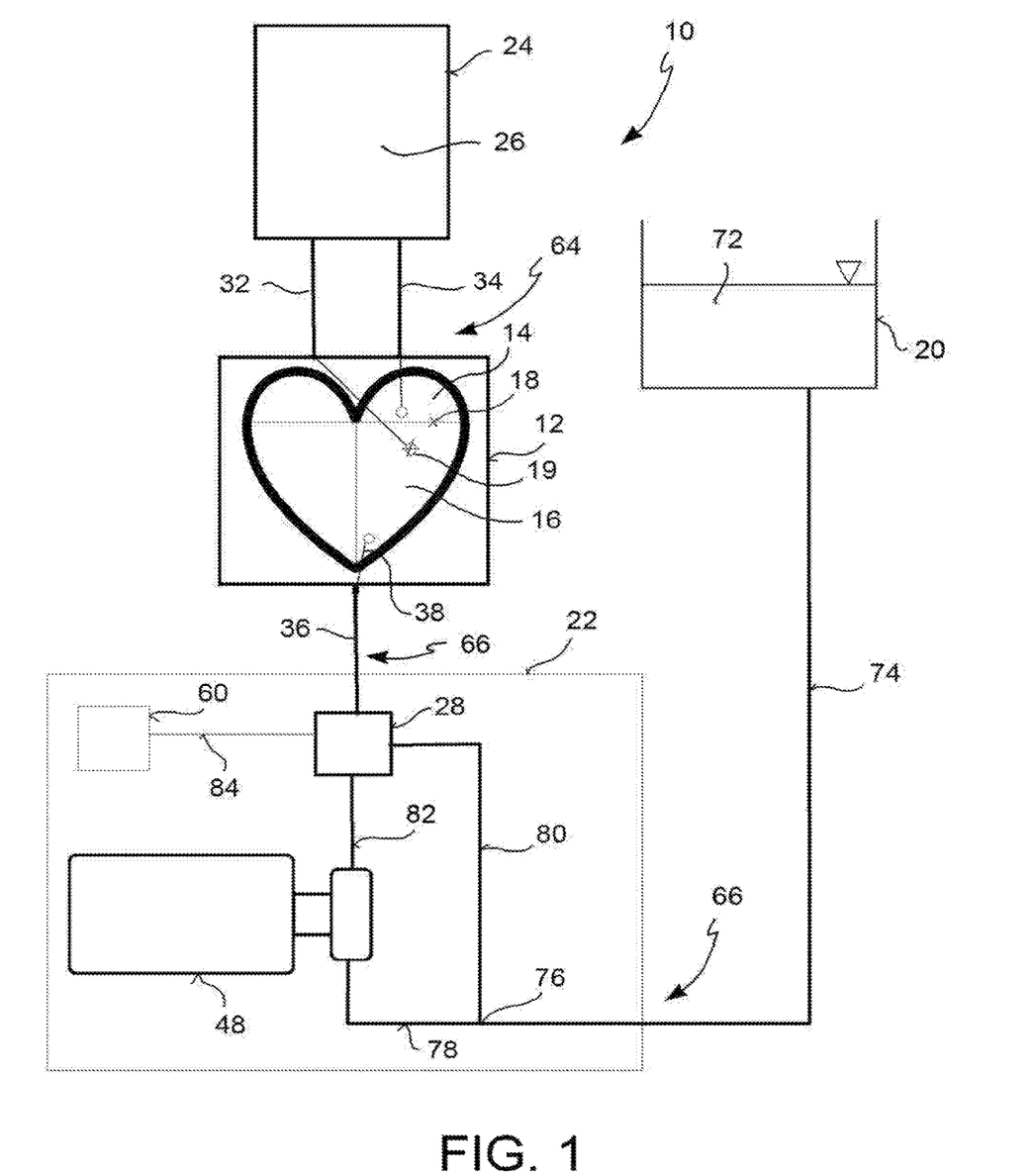
FIG. 1 is a diagrammatic depiction of a test bench assembly, in accordance with one embodiment.
Figure 2:
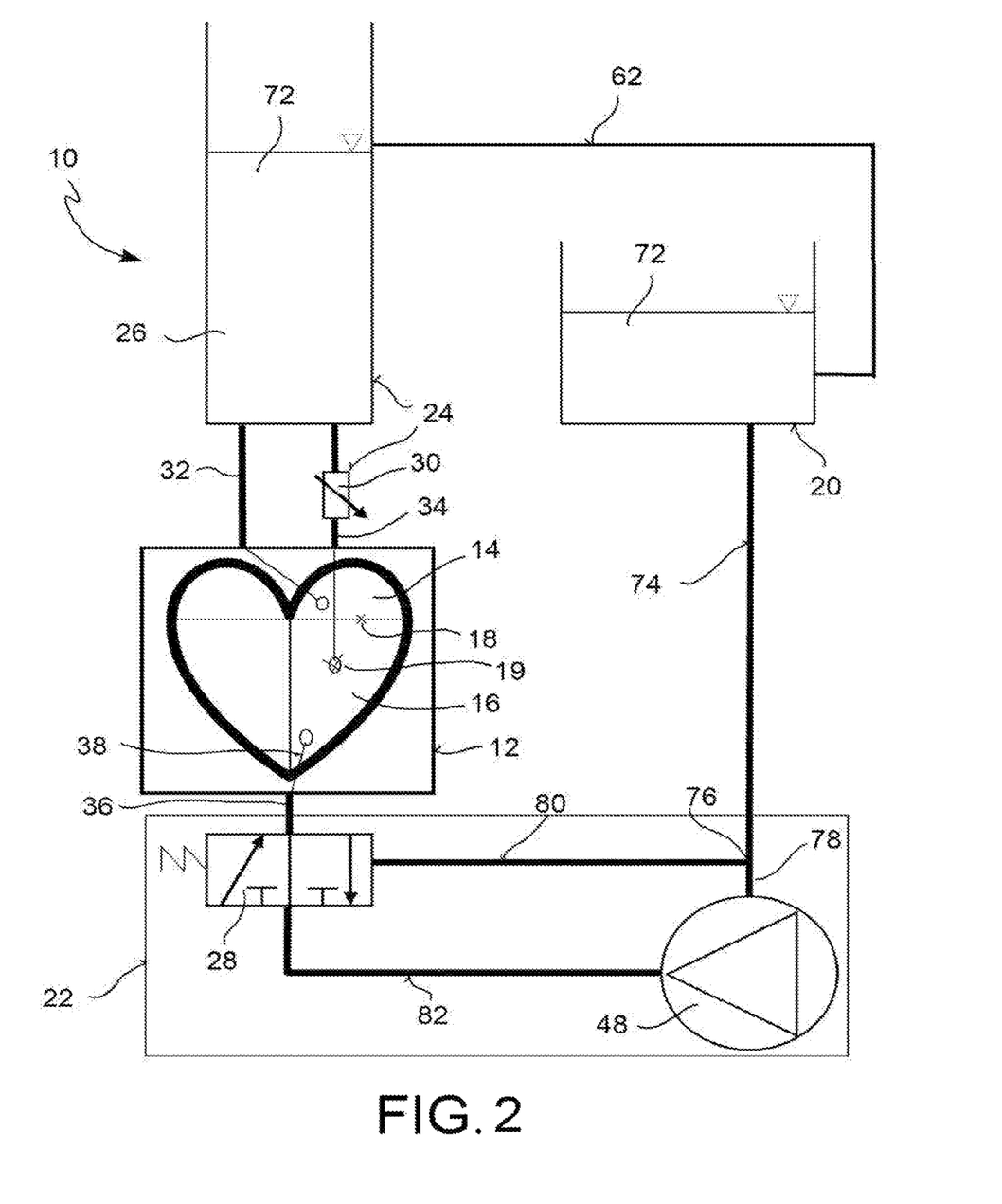
FIG. 2 is a diagrammatic depiction of a test bench assembly, in accordance with one embodiment.
Figure 3:
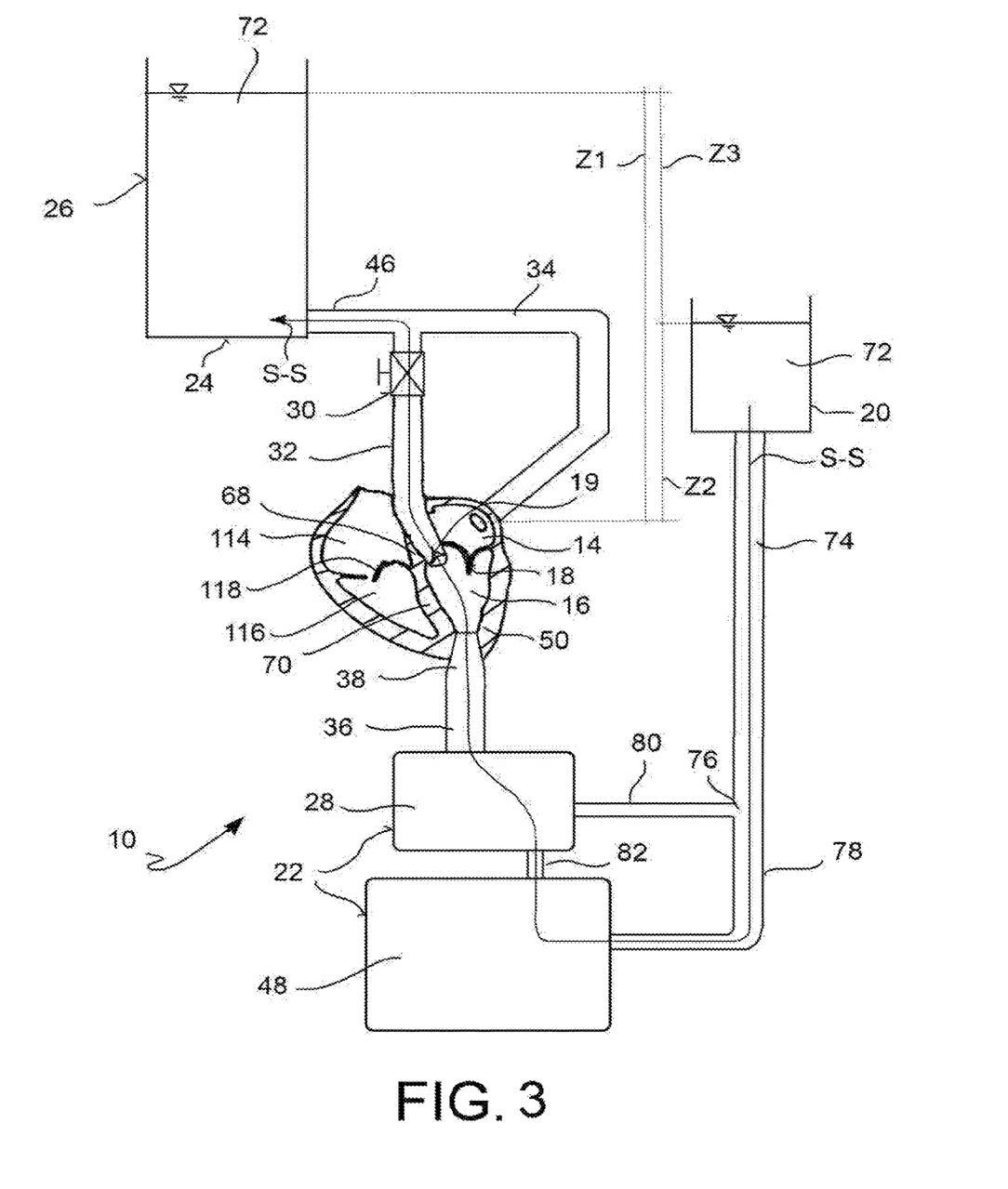
FIG. 3 is a diagrammatic depiction of the operation during the systole phase of a test bench assembly in left heart configuration.

Such a test bench assembly 10 allows to simulate the systolic phase and the diastolic phase. As shown for example in FIG. 3, during the systolic phase, the pressure generator 22, thrusting the working fluid 72 into the ventricular chamber 16; 116, generates a pressure increase in the ventricular chamber 16; 116 which determines the opening of the outflow valve 19, for example the aortic valve 19 in the case of left heart, where present, and thrusts the working fluid 72 towards at least one pressure regulation device 24; 124. In particular, the flow of working fluid 72 passes in the systolic branch 32 of said second fluid connection means 66 and reaches the compliant element 26. The systolic path S-S of the working fluid is indicated with the arrow S-S in FIG. 3.

Figure 4:
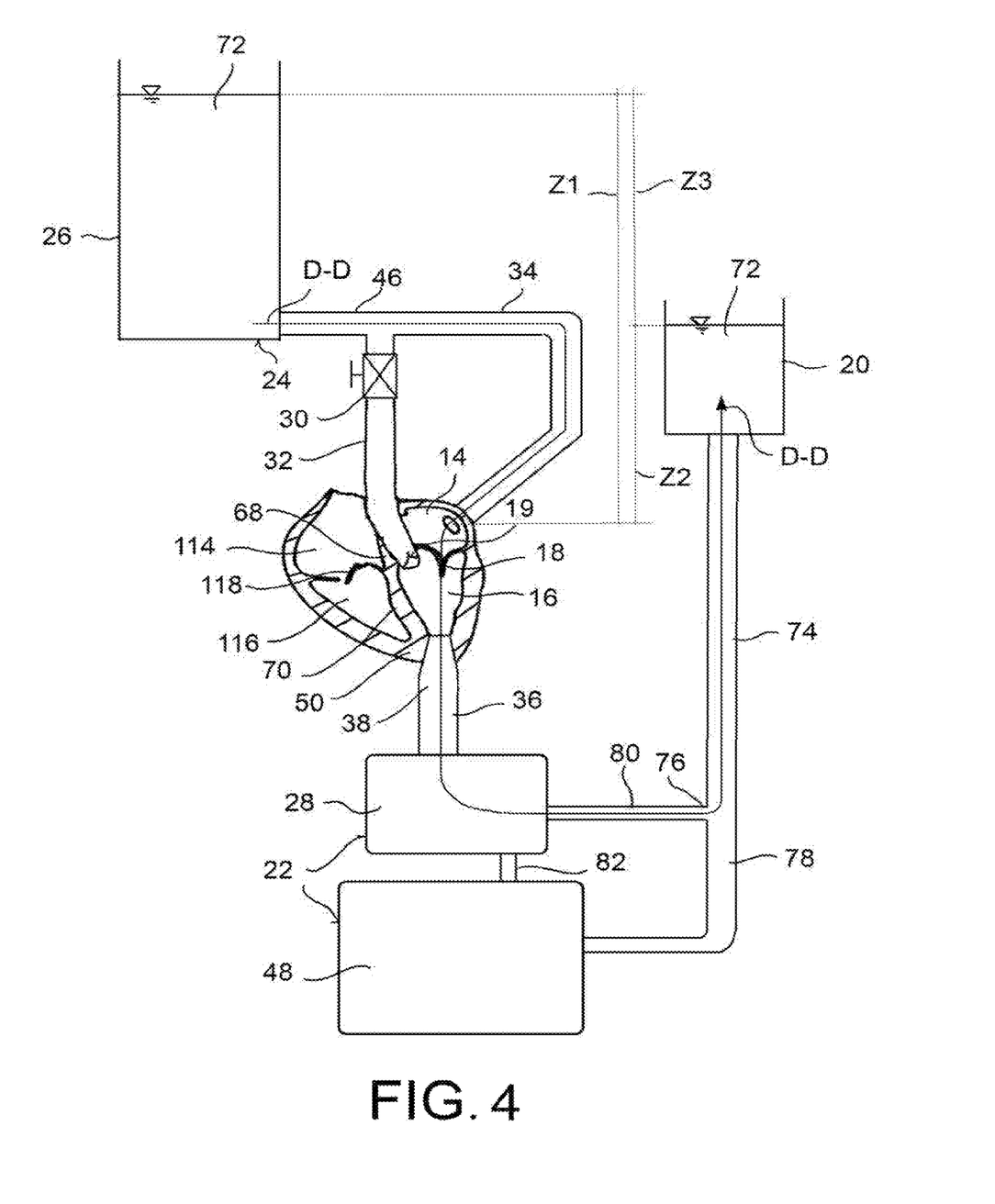
FIG. 4 is a diagrammatic depiction of the operation during the diastole phase of a test bench assembly in left heart configuration.
Figure 5:
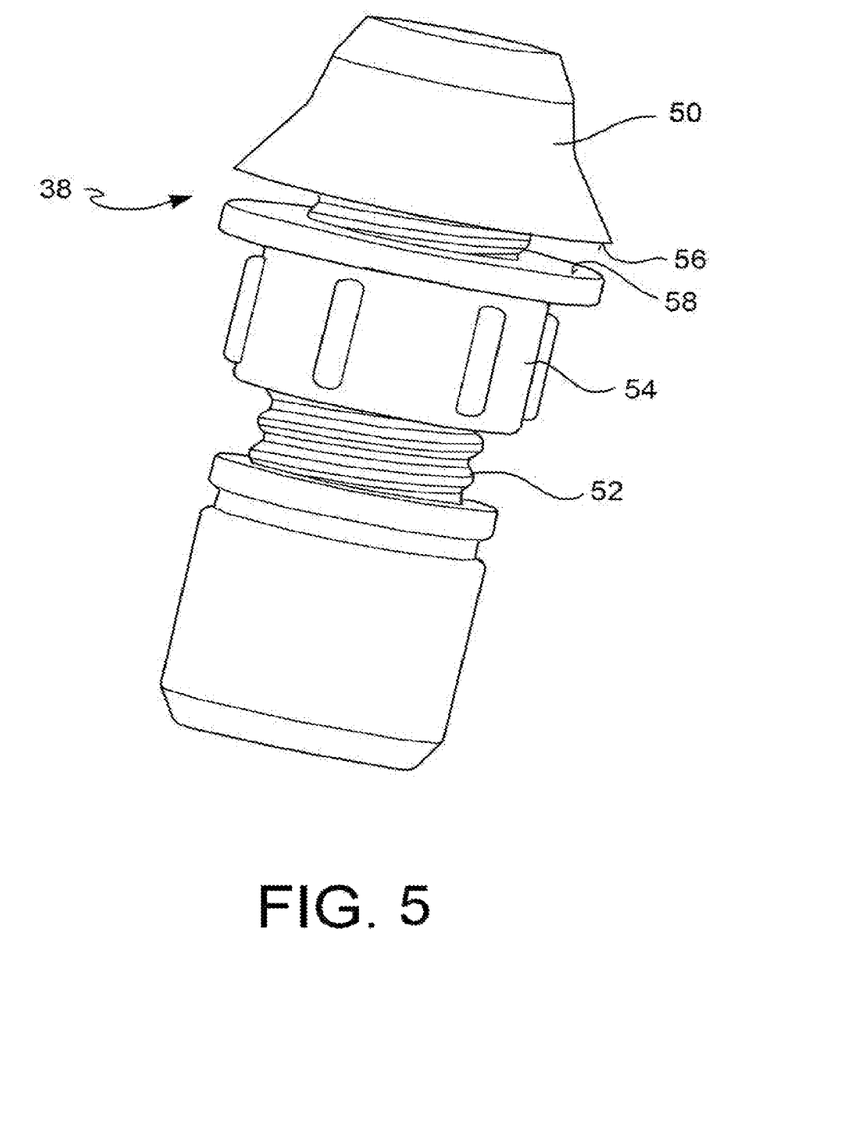
FIG. 5 is an axonometric view of an anchoring plug, in accordance with one embodiment.

As shown for example in FIG. 4, during the diastolic phase, the working fluid 72, by effect of gravity, reaches the atrial chamber 14; 114 raising pressure inside the atrial chamber 14; 114 which determines the opening of the cardiac valve 18; 118, for example the mitral valve in the case of left heart. Hence, the working fluid 72 reaches the ventricular chamber 16; 116 and, again by gravity, traverses the ventricular conduit 36 of said first fluid connection means 66, traverses said flow intercepting element 28, flows through said shunt branch 80 and reaches the reservoir 20 flowing through said reservoir conduit 74. The diastolic path D-D of the working fluid is indicated in FIG. 4 with the arrow D-D.

In accordance with an embodiment in which said passive heart 12 lacks an artificial or natural aortic valve, the provision of said afterload resistance 30 avoids having the diastolic path D-D of the working fluid 72 include the systole branch 32.

In accordance with an embodiment in which said passive heart 12 comprises an artificial or natural aortic valve 19 adapted to direct the path of the working fluid 72 during the diastolic phase, the closure of the aortic valve 19 avoids having the diastolic path D-D include the systole branch 32.

The provision of said flow intercepting element 28, for example a solenoid valve, allows, during the systolic phase, to connect the kinetic stationary flow rate pump 48 to the fluid circuit, and, during the diastolic phase, to disconnect said kinetic stationary flow rate pump 48, to allow the flow towards the reservoir 20. In accordance with an embodiment, the expression "fluid circuit" indicates the useful path through which the working fluid can travel in the test bench assembly 10.

In accordance with one embodiment, said pressure generator 22 comprises a recirculation circuit, which allows, during the diastolic phase, to maintain the kinetic stationary flow rate pump 48 active without thereby increasing pressure within the fluid circuit. The provision of said recirculation circuit allows to obtain a variable flow rate of working fluid 72 within the ventricular chamber 16 without deactivating said stationary flow rate pump 48 cooperating with said flow intercepting element 28.

In accordance with one embodiment, said kinetic stationary flow rate pump 48 is a centrifugal pump. This allows to maintain low the installation costs of the test bench assembly 10, without thereby resulting in a decrease in reliability.

In accordance with an embodiment, said test bench assembly 10 comprises a feedback conduit 62, which connects said compliant element 26 and said reservoir 20, so that, when the working fluid reaches a predefined value of pressure inside said compliant element 26, a portion of the working fluid is sent back into the reservoir 20. This improves the self-regulation of the fluid circuit.

In accordance with an embodiment, said test bench assembly 10 comprises a control and drive unit 60 associated with said pressure generator 22 and comprising at least one programmable logic controller. Preferably, said control and drive unit 60 is adapted to control the activation of the flow intercepting element 28, for example a solenoid valve, to simulate the cardiac cycle. Preferably, said control and drive unit 60 is associated with said pressure generator 22 by means of an electromagnetic connection 84. In accordance with an embodiment, said control and drive unit 60 associated with said pressure generator 22 by means of a wireless electromagnetic connection 84. This allows to control said pressure generator 22 remotely.

In accordance with an embodiment, said test bench assembly 10 comprises an image acquisition system having at least one probe positioned internally to at least one between said atrial cavity 14 and said ventricular cavity 16. Preferably, said image acquisition system comprises a video probe, adapted to acquire a video of the operation of portions of the test bench, for example the operation of at least one cardiac valve 18. Alternatively or additionally, said test bench assembly 10 is suitable for displaying with a fluoroscopy acquisition system, adapted to acquire fluoroscopic images. Alternatively or additionally, said test bench assembly 10 is suitable for displaying with an ultrasound scan acquisition system, adapted to acquire echocardiographic and/or echo Doppler images.

In accordance with a preferred embodiment, said first fluid connection means 64 comprise at least one ventricular conduit 36 which flows into said ventricular chamber 16 of the passive heart 12, and in which said ventricular conduit 36 comprises an anchoring plug 38 which can be fitted by acting only from the exterior of said ventricular chamber 16. The provision of such an anchor plug 38 makes the operation of connecting the passive heart 12 to said first fluid connection means 66 of the test bench quicker compared to known solution, and reliable as well.

In addition, avoiding the need for typically surgical procedures to connect the ventricular conduit 36 to the passive hear 12, for example sutures of the ventricular conduit 36 to the passive heart 12, enables personnel who are not qualified, and hence have lower hourly cost than a cardiac surgeon/interventional cardiologist, to connect the passive heart 12 to the fluid circuit.

In accordance with an embodiment, said anchoring plug 38 comprises a deformable anchoring device 40, adapted to elastically deform to fit into an inlet opening formed in the heart wall 50 which delimits the ventricular chamber 16 of the passive heart 12 to be engaged in undercut against a face of the heart wall 50 arranged in undercut with respect to the outer face of the passive heart. The provision of such an anchoring plug 38 makes the operations for connecting the passive heart 12 to the fluid circuit highly rapid and simple, for example of the "plug-and-play" type. Preferably, said anchoring plug 38 is applied in the apical portion of the passive heart 12.

Preferably, said test bench assembly 10 comprises a collection tank, adapted to collect any fluid leaks. Generally, fluid leaks are prevalently located in the connecting portion between said first fluid connection means 64 and said passive heart 12. The provision of said anchoring plug 38, allowing to avoid connection sutures, allows to significantly reduce fluid leaks compared to known solutions.

In accordance with one embodiment, said anchoring plug 38 comprises a stem 52 which is internally hollow to allow the passage of the working fluid, at least one translating fastening ring nut 54 mounted on said stem 52 and adapted to clamp between the heart wall 50 between a support surface 58 of said ring nut and a fastening surface 56 of said deformable anchoring device 40, to determine the secure anchoring of the anchoring plug 38 to the passive heart 12. In accordance with an embodiment, said stem 52 is externally threaded and said fastening ring nut 54 acts as a translating leadscrew.

In accordance with an embodiment, said anchoring plug 38 comprises a threaded stem which cooperates with a threaded nut delivered into the ventricular chamber 16.

A method for using a test bench shall be described below.

In accordance with a general embodiment, a method for using a test bench assembly for the simulation of cardiac surgery and/or interventional cardiology operations and/or procedures comprises the following steps.
  providing a passive heart 12;
  providing a pressure generator 22;
  providing a reservoir 20 fluidically connected to said pressure generator 22;
  making a hole in the heart wall 50 which delimits a ventricular chamber 18;
  connecting said pressure generator 22 to said passive heart 12;
  using a single compliant element 26 connected to an atrial chamber and a ventricular chamber to provide the working fluid with the preload pressure and the afterload pressure.

In accordance with a possible operating mode, said method comprises the additional step of connecting an anchoring plug 38 to said ventricular chamber 16 through said hole in the heart wall 50 acting only from the exterior of the passive heart 12.

In accordance with a possible operating mode, said method comprises the additional step of using a stationary flow rate pump 48 cooperating with a flow intercepting element 28 to simulate the cardiac flow rate.

Such a test bench assembly 10 is particularly suited, but not univocally intended, to allow in non-invasive manner and with no need to intervene on living being in any way, to train cardiac surgeons/interventional cardiologists on at least one of the following medical-surgical therapies:
  transcatheter aortic valve implantation through a dummy femoral artery;
  transcatheter aortic valve implantation through a dummy ascending aorta;
  transcatheter aortic valve implantation from the left ventricle;
  percutaneous mitral valve implantation from the left ventricle;
  transcatheter implantation of mitral neochordae from the left ventricle;
  percutaneous mitral valve implantation from the fossa ovalis directly or through a virtual vena cava;
  transcatheter mitral valve implantation directly from the left atrium;
  transcatheter introduction of occluder of the left auricle from the interatrial septum directly or through virtual vena cava;
  transcatheter procedures of the tricuspid valve;
  transcatheter procedures of pulmonary valve;
  reparative beating heart surgical procedures.

Thanks to the features described above separately or jointly with each other in particular embodiments, it is possible to obtain a test bench assembly, as well as a method, which at the same time satisfies the mutually contrasting needs described above, and the aforementioned desired advantages, and in particular:
  it is possible to faithfully reproduce the physiological conditions of beating heart and of blood circulation without thereby making the test bench assembly 10 bulky or complicated to operate;
  it is possible to reduce the installation and operation costs of the test bench assembly relative to known solutions, without thereby diminishing functionality or reliability;
  it is possible to reduce the number of components and the size of the test bench assembly relative to known solutions, without thereby diminishing functionality or reliability;
  it is possible to reproduce the physiological conditions of beating heart and blood circulation and at the same time to reduce the costs associated with the procedures to train cardiac surgeons/interventional cardiologists.

Those skilled in the art may make several changes and adaptations to the embodiments described above in order to meet contingent and specific needs, and can replace elements with others which are functionally equivalent, without however departing from the scope of the following claims.

LIST OF REFERENCES

10 Test bench assembly
12 Passive heart

14 Left atrial chamber
16 Left ventricular chamber
18 Mitral heart valve, or mitral valve
19 Outflow valve, or aortic heart valve, or aortic valve
20 Reservoir
22 Pressure generator
24 Pressure regulation device
26 Compliant element
28 Flow intercepting element
30 Afterload resistance
32 Systole branch
34 Diastole branch
36 Ventricular conduit
38 Anchoring plug
40 Deformable anchoring device
46 Section
48 Kinetic stationary flow rate pump
50 Heart wall
52 Stem
54 Fastening ring nut
56 Fastening surface
58 Ring nut support surface
60 Control and drive unit
62 Feedback conduit
64 First fluid connection means
66 Second fluid connection means
68 Atrial septum
70 Ventricular septum
72 Working fluid
74 Reservoir conduit
76 Bifurcation
78 Pump branch
80 Shunt branch
82 Generator conduit
84 Electromagnetic connection
114 Atrial chamber, or right atrial chamber
116 Ventricular chamber, or right ventricular chamber
118 Tricuspid heart valve, or tricuspid valve
124 Additional pressure regulation device
S-S Systole path
D-D Diastole path
z1 First height difference
z2 Second height difference
z3 Third height difference

The invention claimed is:

1. A test bench assembly for simulating cardiac surgery and/or interventional cardiology operations and/or procedures, comprising:
a passive heart, wherein said passive heart is an explanted or artificial or hybrid heart, said passive heart having at least one pair of cardiac chambers comprising an atrial chamber and a ventricular chamber;
a reservoir, adapted to house working fluid;
a pressure generator, adapted to provide said passive heart with a pumping function by pumping said working fluid, said pressure generator being fluidically connected both to said ventricular chamber of said passive heart by at least one ventricular conduit and to said reservoir by a reservoir conduit; and
at least one pressure regulation device which provides the working fluid in input to the atrial chamber with preload pressure and the working fluid in output from the ventricular chamber with afterload pressure;
said at least one pressure regulation device being fluidically connected both to said atrial chamber of said passive heart by a diastole branch and to said ventricular chamber of said passive heart by a systole branch;
wherein said at least one pressure regulation device comprises a single compliant element for each pair of cardiac chambers, said single compliant element providing the working fluid with both preload pressure and afterload pressure.

2. The test bench assembly of claim 1, wherein said single compliant element and said reservoir are distinct elements.

3. The test bench assembly of claim 2, wherein said compliant element comprises a free surface vessel and is positioned higher than said passive heart, which in turn is positioned lower than said reservoir.

4. The test bench assembly of claim 1, wherein said at least one pressure regulation device comprises an afterload resistance which regulates the afterload pressure.

5. The test bench assembly of claim 4, wherein said systole branch comprises said afterload resistance.

6. The test bench assembly of claim 1, wherein said compliant element is selected from the group consisting of: a free surface vessel and a closed pressurized tank.

7. The test bench assembly of claim 1, wherein the working fluid in said compliant element has a higher pressure than the working fluid in said reservoir.

8. The test bench assembly of claim 1, wherein said systole branch and said diastole branch are joined in a section which flows into said compliant element.

9. The test bench assembly of claim 1, wherein said pressure generator comprises at least one flow intercepting element, and wherein the at least one flow intercepting element selectively allows direct fluid connection between said passive heart and said reservoir.

10. The test bench assembly of claim 9, wherein said at least one flow intercepting element comprises at least one active valve.

11. The test bench assembly of claim 10, wherein said at least one active valve comprises at least one solenoid valve.

12. The test bench assembly of claim 1, wherein said pressure generator comprises a kinetic stationary flow rate pump.

13. The test bench assembly of claim 12, wherein said kinetic stationary flow rate pump comprises a centrifugal pump.

14. The test bench assembly of claim 1, wherein said ventricular conduit comprises an anchoring plug which is fitted by acting only from an exterior of said ventricular chamber.

15. The test bench assembly of claim 14, wherein said anchoring plug comprises a deformable anchoring device adapted to elastically deform to fit into an inlet opening formed in the heart wall which delimits the ventricular chamber of the passive heart to be engaged in undercut against a face of the heart wall arranged in undercut with respect to an outer face of the passive heart.

16. The test bench assembly of claim 1, comprising a control and drive unit associated with said pressure generator and comprising at least one programmable logic controller.

17. The test bench assembly of claim 1, wherein said passive heart comprises at least an outlet of said ventricular chamber of said at least one pair of cardiac chambers;
wherein said afterload pressure provided to the working fluid in output from the ventricular chamber is downstream said at least an outlet of said ventricular chamber,
wherein said at least one pressure regulation device is fluidically connected both to said atrial chamber of said passive heart by a diastole branch and to said ventricular chamber of said passive heart through said at least an outlet of said ventricular chamber by a systole branch.

18. The test bench assembly of claim 17, wherein said passive heart further comprises at least one outflow valve positioned at said an outlet of said ventricular chamber.

19. The test bench assembly of claim 18, wherein said outflow valve is selected from the group consisting of: an aortic valve and a pulmonary valve.

20. The test bench assembly of claim 1, wherein said single compliant element acts as an expansion vessel.

21. The test bench assembly of claim 1, wherein said test bench assembly comprises a feedback conduit, which connects said compliant element and said reservoir, so that, when the working fluid reaches a predefined value of pressure inside said compliant element, a portion of the working fluid is sent back into the reservoir.

\* \* \* \* \*